(12) United States Patent
Vago et al.

(10) Patent No.: US 9,174,945 B2
(45) Date of Patent: *Nov. 3, 2015

(54) ROSUVASTATIN ZINC SALT

(75) Inventors: Pal Vago, Budapest (HU); Gyula Simig, Budapest (HU); Gyoergy Clementis, Budapest (HU); Peter Toempe, Budapest (HU); Sandorne Tapai, Gyoemroe (HU)

(73) Assignee: EGIS GYOGYSZERGYAR NYILVANOSAN MUKODO RESZVENYTARSASAG, Budapest (HU)

( * ) Notice: Subject to any disclaimer, the term of this patent is extended or adjusted under 35 U.S.C. 154(b) by 1314 days.

This patent is subject to a terminal disclaimer.

(21) Appl. No.: 12/296,976

(22) PCT Filed: Apr. 12, 2007

(86) PCT No.: PCT/HU2007/000030
§ 371 (c)(1),
(2), (4) Date: Apr. 14, 2009

(87) PCT Pub. No.: WO2007/119085
PCT Pub. Date: Oct. 25, 2007

(65) Prior Publication Data
US 2009/0306117 A1 Dec. 10, 2009

(30) Foreign Application Priority Data
Apr. 13, 2006 (HU) .................................... 0600293

(51) Int. Cl.
C07D 239/42 (2006.01)

(52) U.S. Cl.
CPC ................................. C07D 239/42 (2013.01)

(58) Field of Classification Search
CPC .................................................... C07D 239/42
USPC ........................................................ 544/297
See application file for complete search history.

(56) References Cited

U.S. PATENT DOCUMENTS

| 4,440,691 | A | * | 4/1984 | Kuzuna et al. ................ 556/132 |
| 5,091,547 | A | * | 2/1992 | Buxade ........................ 556/131 |
| 5,260,440 | A | * | 11/1993 | Hirai et al. .................... 544/332 |
| 5,310,936 | A | * | 5/1994 | Regtop et al. ................. 548/501 |
| 5,686,104 | A | | 11/1997 | Mills et al. |
| 6,316,460 | B1 | | 11/2001 | Creekmore et al. |
| 7,642,287 | B2 | | 1/2010 | Guzman et al. |
| 8,507,513 | B2 | * | 8/2013 | Kovanyine Lax et al. .... 514/275 |
| 2003/0045718 | A1 | | 3/2003 | Taylor et al. .................. 544/327 |
| 2003/0175338 | A1 | | 9/2003 | Singh et al. |
| 2004/0009997 | A1 | | 1/2004 | Taylor ........................... 514/275 |
| 2004/0034038 | A1 | | 2/2004 | Li et al. ......................... 514/255 |
| 2005/0038012 | A1 | * | 2/2005 | Eerden et al. ............. 514/212.07 |
| 2005/0131055 | A1 | | 6/2005 | Radl et al. ..................... 514/423 |
| 2005/0131066 | A1 | | 6/2005 | Niddam-Hildesheim et al. ............... 514/548 |
| 2005/0148646 | A1 | | 7/2005 | Boykin et al. ................ 514/394 |
| 2006/0034815 | A1 | | 2/2006 | Guzman et al. .............. 424/94.1 |
| 2008/0221323 | A1 | | 9/2008 | Crabb et al. .................. 544/297 |
| 2013/0338360 | A1 | * | 12/2013 | Kovanyine Lax et al. .... 544/332 |

FOREIGN PATENT DOCUMENTS

| WO | WO 2005019170 A1 | * | 3/2005 |
| WO | WO 2005/115980 | | 12/2005 |
| WO | WO-2005123082 | | 12/2005 |
| WO | WO 2005123082 A1 | * | 12/2005 |
| WO | WO 2009/157014 A2 | | 12/2009 |

OTHER PUBLICATIONS

English Translation of WO 2005/123082 (Dec. 2005).*
L.D. Bighley et al., Salt Forms and Absorption, in 13 Encyclopedia of Pharmaceutical Technology 453 (M Swarbrick and J. Boylan eds., 1996).*
S. H. Neau, Pharmaceutical Salts, in Water-Insoluble Drug Formulation 417, 429 (R. Liu ed., CRC Press, 2008).*
S. Badaway et al., Salt Selection for Pharmaceutical Compounds, in Preformulation in Solid Dosage Form Dev. 63 (M. Adeyeye ed., 2008).*
R.J. Bastin et al., Salt Selection and Optimization Procedures for Pharmaceutical New Chemical Entities, 4 Organic Process Res. Dev. 427 (2000).*
Gould, Salt Selection for Basic Drugs, 33 Int. J. Therapeutics 201, 217 (1986).*
K. R. Morris et al., An Integrated Approach to the Selection of Optimal Salt Form for a New Drug Candidate, 105 Int'l. J. Pharm. 209 (1994).*
K. Chow et al., Engineering of Pharmaceutical Materials: an Industrial Perspective, 97 J. Pharmaceutical Sciences, 2855 (2008).*

(Continued)

Primary Examiner — Alexander R Pagano
(74) Attorney, Agent, or Firm — Lucas & Mercanti, LLP; Jonathan Myers

(57) ABSTRACT

The present invention is related to rosuvastatin zinc salt of the Formula (I), process for preparation thereof and medicinal products containing said salt. Rosuvastatin zinc salt according to the present invention is prepared by reacting rosuvastatin with a zinc alcoholate, zinc enolate or an inorganic or organic zinc salt and isolating the thus obtained rosuvastatin zinc salt (2:1).

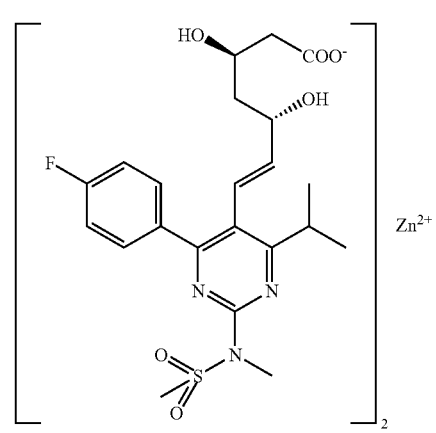

3 Claims, No Drawings

(56) References Cited

OTHER PUBLICATIONS

Singh et al, 22 Journal of Microencapsulation 761-771, (2005).*
Graul et al:"Atorvastatin Calcium", Drugs of the Future, Barcelona, ES, vol. 22, No. 9, 1997, pp. 956-968.
Database WPI, Derwent Publications Ltd, London, GB; AN 2006-08959 XP002448430; Zhao Zhiquan [CN]: "An Anti-hyperlipemia position".

K.R. Morris et al; An integrated approach to the selection of optimal salt . . . ; Int. Journ of Pharm 105 (1994) 209-217.
E5: Int. Journ. Phar.; 105; 1994; pp. 209-217; K. Morris et al; An integrated approach to the selection of optimal . . . .
Excerpts from Handbook Pharmaceutical Salts, P. Heinrich Stahl, et al; pp. 334-335, 342.

* cited by examiner

ROSUVASTATIN ZINC SALT

CROSS REFERENCE TO RELATED APPLICATIONS

This application is the US national phase of PCT application PCT/HU2007/000030, filed 12 Apr. 2007, published 25 October 2007 as WO 2007/119085, and claiming the priority of Hungarian patent application P0600293 itself filed 13 Apr. 2006, whose entire disclosures are herewith incorporated by reference.

FIELD OF THE INVENTION

The present invention relates to the zinc salt of (+)-7-[4-(4-fluorophenyl)-6-isopropyl-2-(N-methyl-N-methyl-sulphonylamino)pyrimidin-5-yl]-(3R,5S)-dihydroxy-(E)-6-heptenecarboxylic acid of the Formula (I),

I

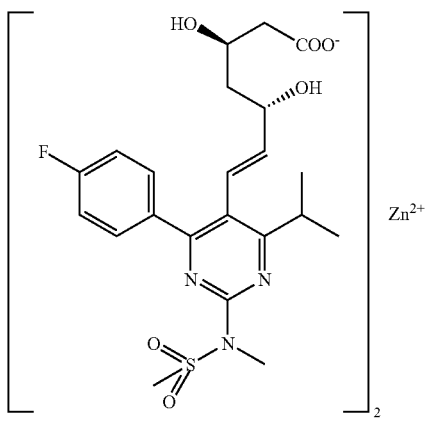

its hydrates, process for their preparation, medicinal products containing said salts, process for the preparation of medicinal products and the use of said salts in the medicine.

(+)-7-[4-(4-fluorophenyl)-6-isopropyl-2-(N-methyl-N-methyl-sulphonyl-amino)-pyrimidin-5-yl]-(3R,5S)-dihydroxy-(E)-6-heptene-carboxylic acid of the Formula (II)

II

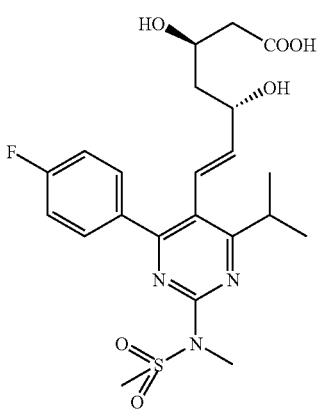

is known under the International Nonproprietary Name (INN) rosuvastatin.

TECHNICAL BACKGROUND OF THE INVENTION

Rosuvastatin of the Formula (II) has been disclosed for the first time in European Patent No. 521471. The calcium salt of rosuvastatin is used in the medicine for the treatment of hypercholesterolemia, hyperlipoproteinemia and atherosclerosis.

The health authorities are setting strict quality criteria towards pharmaceutically active ingredients. Some of these criteria are related to the chemical purity and stability of the pharmaceutically active ingredients. Other official requirement is the manufacture of the medicinal product in satisfactory quality and that the medicinal product shall have appropriate stability. Such criteria are determined by and published in the corresponding articles of pharmacopoeias.

In the case of rosuvastatin of the Formula (II), basic requirements for the active pharmaceutical ingredient intended for the use in medicinal products are high purity, appropriate stability and the possibility of simple formulation.

According to published International Patent Application No. WO 00/042024, the amorphous rosuvastatin of the Formula (II) obtained according to the process of European Patent No. 521471 can be used in the pharmaceutical technology with great difficulties. In order to eliminate this disadvantage, crystalline forms having more advantageous physical properties than the amorphous product are prepared. The manufacture of crystalline rosuvastatin calcium salt, however, is a manufacturing process requiring high production volume and results in great loss of material.

The basic problem in the manufacture of the calcium salt of rosuvastatin resides in the fact that the primary product obtained is poorly filterable and can not be purified in an easy way. Published International Patent Application WO 04/14872 discloses non-crystalline product having advantageous filterability. According to the process of said application, the calcium salt of advantageous particle size is prepared by reacting an alkaline metal, ammonium, methylammonium or tris(hydroxymethyl)-methylammonium salt of rosuvastatin with calcium chloride in an aqeuous solution.

In the published International Patent Application No. WO 01/60804, there are disclosed high purity ammonium-, lithium- or magnesium salts of rosuvastatin of the Formula (II) in order to solve production problems which arose during the manufacture of amorphous rosuvastatin. Starting from the above-mentioned salts, it is possible to prepare amorphous rosuvastatin in a quality suitable for the manufacture of medicinal products.

Published International Patent Application WO 2005/051921 discloses a similar process, wherein isopropylammonium or cyclohexylammonium salts of rosuvastatin are produced in high purity and said salts are transformed into sodium salt or high purity amorphous calcium salt of rosuvastatin.

Published International Patent Application No. WO 2005/040132 discloses amorphous rosuvastatin calcium salt of high diastereomeric purity. According to the disclosed process, the primary product amorphous rosuvastatin calcium salt is crystallized in the first stage, the product thus obtained is subsequently transformed into the amorphous form.

In summary, it can be concluded that according to the state of the art, the manufacture of rosuvastatin calcium salt suitable for the preparation of medicinal products is a particularly intricate process. The crude product must be submitted to further purification and crystallization steps in order to obtain a suitable product with regard to purity and physical properties. The known processes are difficult to operate in an industrial scale process and the use of such known processes often results in a significant loss of material and is therefore uneconomical.

SUMMARY OF THE INVENTION

The objective of our research-development work was to develop a new salt of [(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid of the Formula (II) having high stability which maintains or enhances the pharmacological effect characteristic to the group of statins and which can be prepared in a quality suitable for the manufacture of medicinal products.

The above objective is solved according to the present invention.

The basis of the present invention is the surprising recognition that the zinc salt of (+)-7-[4-(4-fluorophenyl)-6-isopropyl-2-(N-methyl-N-methyl-sulphonylamino)pyrimidin-5-yl]-(3R,5S)-dihydroxy-(E)-6-heptenecarboxylic acid of the Formula (I) and its hydrated forms satisfy all the above criteria, since said salt is suitable for the production of medicinal products, has excellent stability towards heat and light and can be produced in high purity by industrially convenient processes.

DETAILED DESCRIPTION OF THE INVENTION

According to the first aspect of the present invention, there is provided the rosuvastatin zinc salt of the Formula (I), which can be prepared in high purity directly suitable for the manufacture of medicinal products. Rosuvastatin zinc salt of the Formula (I) is new.

The advantage of the rosuvastatin zinc salt of the Formula (I) compared to the calcium salt of rosuvastatin known according to the state of the art resides in the fact that the zinc salt can be prepared in high quality, by a simple process which can be easily scaled up to industrial production. Further advantage of the rosuvastatin zinc salt is that it can be manipulated very easily and that the pre-treatment of the primary product for pharmaceutical formulation does not require further processing.

Rosuvastatin zinc salt of the Formula (I) is stable towards heat and light, which is an advantage during pharmaceutical processing, formulation and during the use as medicine. The product can be advantageously used for the treatment of the disorders of lipid metabolism, such as hypercholesterolemia, hyperlipoproteinemia and atherosclerosis.

According to the second aspect of the present invention, there is provided a process for the preparation of rosuvastatin zinc salt of the Formula (I), which comprises reacting rosuvastatin of the Formula (II) with a zinc compound.

According to the first process variant suitable for the preparation of rosuvastatin zinc salt of the Formula (I), (+)-7-[4-(4-fluorophenyl)-6-isopropyl-2-(N-methyl-N-methyl-sulphonyl-amino)pyrimidin-5-yl]-(3R,5S)-dihydroxy-(E)-6-heptenecarboxylic acid of the Formula (II) is reacted with a zinc alcoholate and the rosuvastatin zinc of the Formula (I) thus obtained is isolated.

As zinc alcoholate, a compound of the Formula (III)

R—O—Zn—O—R    III wherein R represents a straight or branched-chain alkyl group comprising 1 to 4 carbon atoms, can be used in a 0.5 to 0.6 molar equivalent amount calculated on the basis of the molar amount of rosuvastatin of the Formula (II).

The reaction is carried out in a solvent. Suitable solvents are aliphatic alcohols comprising 1 to 4 carbon atoms, e.g. methanol, ethanol, 2-propanol or 1-butanol; aliphatic ketones comprising 3 to 8 carbon atoms; aliphatic esters comprising 2 to 8 carbon atoms or aliphatic ethers comprising 4 to 8 carbon atoms or the mixtures thereof.

The preparation of the salt is carried out at a temperature between room temperature and the boiling temperature of the solvent, preferably at a temperature between 25 and 50° C.

The product is isolated by evaporating the solvent. Optionally the solution can be treated with silica gel before the solvent evaporation. The evaporation residue is triturated with a large excess of an ether comprising 4 to 8 carbon atoms, preferably with diethyl ether and the solids thus obtained are filtered.

A second possibility to isolate the product is dissolving the evaporation residue obtained without silica treatment in an aliphatic ester comprising 2 to 8 carbon atoms and treating the thus obtained solution with silica. After repeated filtration, the solvent is partly evaporated and the residue is stirred with a large excess of an ether comprising 4 to 8 carbon atoms, preferably with diethyl ether and the precipitated product is filtered.

According to the second process variant, rosuvastatin of the Formula (II) is reacted with a zinc enolate of the Formula (IV).

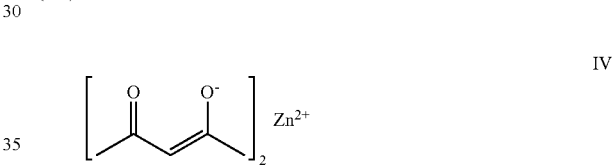

IV

The zinc enolate of the Formula (IV) is used in a 0.5 to 0.6 molar equivalent amount calculated on the basis of the molar amount of rosuvastatin of the Formula (II).

The reaction of the compounds of the Formulae (II) and (IV) is performed in a solvent. Suitable solvents are aliphatic alcohols comprising 1 to 4 carbon atoms. The reaction can be carried out at a temperature between room temperature and the boiling temperature of the solvent, preferably between 25-40° C.

The product can be isolated by treating the solution with silica, filtering, concentrating the solution by evaporating the solvent and precipitating the product by adding a large excess of an ether comprising 4 to 8 carbon atoms, preferably by the addition of diethylether.

According to the third variant for the preparation of rosuvastatin zinc salt of the Formula (I), the alkali metal salt of (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid of the Formula (II) is reacted with an inorganic or organic zinc salt and the thus obtained product of the Formula (I) is isolated.

In the process, zinc salts of inorganic or organic acids can be used. Preferable zinc salts are zinc chloride, zinc sulfate or zinc acetate.

The starting substance is preferably the sodium salt of the compound of the Formula (II).

The reaction can be carried out in water using a water-soluble zinc salt, e.g. zinc chloride, zinc sulfate or zinc acetate. The reaction can also be carried out in organic solvents, e.g. in aliphatic alcohols comprising 1 to 4 carbon atoms; in ketones comprising 3 to 10 carbon atoms including acetone or in aliphatic nitriles, such as acetonitrile. The above-mentioned solvent can be used in the form of mixtures with each other or with water.

According to a preferable embodiment of the process, zinc chloride dissolved in ethanol or in water or zinc sulfate dissolved in water are used and the reaction is carried out at a temperature between 25 and 50° C.

According to the particularly preferable embodiment of the present invention, the sodium salt of rosuvastatin of the Formula (II) is reacted with a 0.5 molar equivalent amount of zinc sulfate in an aqueous solution at a temperature between 25 to 40° C. The product is isolated from the aqueous reaction mixture either by filtration or by washing out the product from the aqeuous solution using a water-immiscible solvent. Subsequently the organic phase is separated, concentrated to a small volume and the rosuvastatin zinc salt of the Formula (I) is isolated.

Advantageous water-immiscible solvents for the extraction of rosuvastatin zinc salt of the Formula (I) are aliphatic esters comprising 2 to 8 carbon atoms, which are good solvents for rosuvastatin zinc salt, e.g. ethylformate, ethylacetate or methylacetate. Rosuvastatin zinc salt of the Formula (I) is isolated by concentrating the extract to a small volume and precipitating rosuvastatin zinc salt by addition of an ether comprising 4 to 8 carbon atoms, preferably diethylether.

The rosuvastatin zinc salt according to the present invention is similar to other rosuvastatin salts known according to the state of the art, for example, the calcium salt in the respect that none of them have definite melting temperature. Therefore the rosuvastatin zinc salt according to the present invention is characterized in the examples by the starting temperature of the melting.

Furthermore it has been found that the zinc salt of rosuvastatin according to the present invention can be obtained in anhydrous as well as in hydrated form. Rosuvastatin zinc salt of the Formula (I) is generally obtained in the form of hydrate in the case when the solvent used during the preparation thereof in an aqueous solvent or solvent mixture. In the case, however, when organic solvents were used during the salt formation reaction, the anhydrous form is produced.

According to a further aspect of the present invention, there are provided medicinal products comprising rosuvastatin zinc salt of the Formula (I) in admixture with one or more pharmaceutically acceptable vehicles or auxiliary agents.

The medicinal products according to the present invention generally contain the active pharmaceutical ingredient in the concentration of 0.1 to 95 percent by weight, preferably, 1 to 50 percent by weight, the most advantageously 5 to 30 percent by weight.

The medicinal products according to the present invention can be administered orally (e.g. in the form of powders, tablets, coated tablets, chewing tablets, capsules, microcapsules, granules, dragees, lozenges, solutions, suspensions or emulsions), parenterally (e.g. as intravenous, intramuscular or intraperitoneal injections or in the form of infusions), rectally (as suppositories or retention enemas), transdermally (e.g. as patches), in the form of implants or can be administered topically (e.g. in the forms of ointments, creams or patches). The solid, semisolid or liquid medicinal preparations containing the rosuvastatin zinc salt of the Formula (I) can be prepared according to the methods of pharmaceutical technology known according to the state of the art.

Solid medicinal products containing rosuvastatin zinc salt of the Formula (I) prepared for oral administration can contain vehicles or filling agents (e.g. lactose, glucose, starch, calcium phosphate, microcrystalline cellulose), binding agents (e.g. gelatine, sorbitol, polyvinylpyrrolidone), disintegrants (e.g. croscarmellose, sodium carboxymethylcellulose, crospovidone), tabletting aids (e.g. magnesium stearate, talc, polyethyleneglycols, silicic acid, silica, silicon dioxide) and surfactants (e.g. sodium laurylsulfate). Liquid medicinal products containing rosuvastatin zinc salt of the Formula (I) suitable for oral administration can be prepared in the form of solutions, syrups, suspensions or emulsions and can contain suspending agents (e.g. gelatine, carboxymethylcellulose), emulsifiers (sorbitane monooleate), solvents (e.g. water, oils, glycerol, propylene glycol, ethanol), buffers (e.g. acetate, phosphate, citrate buffer) or stabilizers (e.g. methyl-4-hydroxy-benzoate).

Liquid medicinal products containing rosuvastatin zinc salt of the Formula (I) prepared for parenteral use are sterile isotonic solution, which can contain conserving agents and buffers besides the solvent.

Semisolid medicinal products containing rosuvastatin zinc salt of the Formula (I), e.g. suppositories contain the active ingredient homogeneously dispersed in the vehicle (e.g. polyethylene glycol or coca butter) of the preparation.

Medicinal products containing rosuvastatin zinc salt according to the present invention as active ingredient contain said compound as unit dosage forms.

A further aspect of the present invention is the use of rosuvastatin zinc salt of the Formula (I) for the manufacture of medicines.

The medicinal products containing rosuvastatin zinc salt according to the present invention can be produced using the methods of pharmaceutical technology known from the state of the art. The active ingredient is admixed with solid or liquid pharmaceutically acceptable vehicles or auxiliary agents and the mixture is brought to a pharmaceutical dosage form. The methods and pharmaceutically acceptable vehicles or auxiliary agents are known from the literature (Remington's Pharmaceutical Sciences, Edition 18, Mack Publishing Co., Easton, USA, 1990).

A further aspect of the present invention is a method for the treatment of hyperlipoproteinemia, hypercholesterolemia and atherosclerosis, which comprises administering the patient in need of such treatment the rosuvastatin zinc salt according to the present invention in a clinically effective dose.

Further details of the present invention are disclosed in the following examples without limiting the invention itself to said examples.

EXAMPLE 1

(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic Acid Zinc Salt (2:1)

4.16 mmol (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid are dissolved in 70 ml methanol and 0.60 g (2.13 mmol) zinc acetylacetonate monohydrate are added to this solution at room temperature. The reaction mixture is stirred at room temperature for eight hours. After this period, 1.0 g of silica are added and the reaction mixture is stirred for 30 minutes. The mixture is filtered and the filtrate is concentrated to one-tenth volume by evaporating the solvent. The residue is mixed with 20-fold volume of diethylether, the precipitate is filtered, washed with diethylether and dried at 40° C. in vacuo. Thus 2.05 g (93%) product is obtained, which starts melting at the temperature of 137° C.

IR (KBr): 3423, 1546, 1381, 1156 $cm^{-1}$.

HNMR (DMSO-$d_6$, 500 MHz): δ 7.72 (dd, J=5.9 Hz, 7.7 Hz, 2H), 7.27 (t, J=8.5 Hz, 2H), 6.52 (d, J=15.9 Hz, 1H), 5.54 (dd, J=5.1 Hz, 15.9 Hz, 1H), 4.94 (b, 2H), 4.21 (m, 1H), 3.84 (m, 1H), 3.55 (s, 3H), 3.46 (s, 3H), 3.40 (m, 1H), 2.26 (d,

J=13.7 Hz, 1H), 2.16 (dd, J=7.7 Hz, 14.5 Hz, 1H), 1.52 (m, 1H), 1.38 (m, 1H), 1.22 (d, J=6.4 Hz, 6H) ppm.

EXAMPLE 2

(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic Acid Zinc Salt (2:1)

3.85 g (8.0 mmol) (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid are dissolved in 40 ml of ethylacetate and to this solution are added the solution of 0.62 g (4.0 mmól) zinc ethylate in 40 ml of ethanol. The reaction mixture is refluxed for two hours. The reaction mixture is cooled, filtered and the solvent is evaporated. The residue is triturated with 50 ml of diethylether. The suspension is filtered, the solids are dissolved in 50 ml of ethylacetate and the solution is stirred with 2 g of silica gel for three hours. The silica gel is filtered off, two-third volume of the solvent is evaporated and the residue is stirred in with tenfold volume of diethylether. The precipitated zinc salt is filtered, washed with diethylether and dried. Thus 2.8 g (68%) of rosuvastatin zinc salt is obtained which starts melting 137° C.

EXAMPLE 3

(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic Acid Zinc Salt (2:1)

The process disclosed in Example 2 is followed with the difference that the reaction is carried out by stirring the reaction mixture at room temperature for sixteen hours. Thus 3.0 g (73%) of rosuvastatin zinc salt are obtained.

EXAMPLE 4

(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic Acid Zinc Salt (2:1)

4.16 mmol (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid are dissolved in 70 ml of ethylacetate and to this solution, 4.2 ml (1.0 mmol/ml) freshly prepared ethanolic sodium ethylate solution are added at room temperature. Under continuos stirring, the solution of 2.0 mmol zinc chloride prepared in 10 ml of ethanol are added over a period of 30 minutes. The reaction mixture is stirred for two hours at 50° C., then cooled to room temperature and filtered. The filtrate is evaporated to one-tenth volume and the product is precipitated with tenfold volume of diethylether. Subsequently, the product is filtered and dried at 50° C. Thus 1.8 g (86%) of rosuvastatin zinc salt are obtained, which starts melting at 136° C.

EXAMPLE 5

(+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic Acid Zinc Salt (2:1)

The title compound is prepared according to the process of Example 4 with the modification that the reaction is carried out at room temperature. Thus 1.65 g (77%), of the title compound are obtained, which starts melting at 137° C.

EXAMPLE 6

(+)-7-[4-(4-fluorophenyl)-6-isopropyl-2-methyl-N-methylsulphonyl-amino)pyrimidin-5-yl]-(3R,5S)-dihydroxy-(E)-6-heptenecarboxylic Acid Zinc Salt (2:1)

The title compound is prepared according to the process of Example 4 with the difference that as reagent, 2.0 mmol zinc sulphate dissolved in water are used and the reaction is performed at room temperature. After separation of the aqeuous layer, the product is isolated by evaporating two-third of the solvent and triturating the residue in tenfold volume of diethylether. The precipitated solid is filtered and dried at the temperature of 50° C. Thus 1.76 g (81%) of rosuvastatin zinc salt are obtained, which starts melting at 138° C.

What is claimed is:

1. Medicinal products containing (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid zinc salt (2:1) of the formula (I) in admixture with one or more pharmaceutically acceptable vehicle or auxiliary agent.

2. A process for the preparation of medicinal products according to claim 1, which comprises mixing (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid zinc salt (2:1) of the formula (I) with pharmaceutically acceptable vehicles or auxiliary agents and transforming the mixture into a pharmaceutical dosage form.

3. (+)-7-[4-(4-fluorophenyl)-6-isopropyl-2-(N-methyl-N-methylsulphonyl-amino)pyrimidin-5-yl]-(3R,5S)-dihydroxy-(E)-6-heptenecarboxylic acid zinc salt (2:1) of the formula (I)

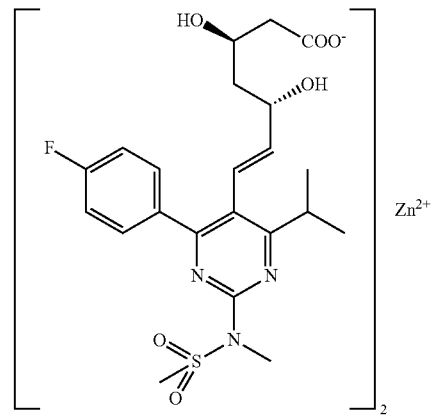

or a hydrate thereof.